United States Patent [19]

Brisset et al.

[11] Patent Number: 4,568,360

[45] Date of Patent: Feb. 4, 1986

[54] MIXED ORGANOMETALLIC COMPOSITIONS COMPRISING ELEMENTS FROM THE LANTHANIDE GROUP AND MANGANESE OR ELEMENTS FROM THE IRON GROUP, PROCESS FOR THE PREPARATION OF SAID COMPOSITIONS, AND THEIR USE AS FUEL ADDITIVES

[75] Inventors: Guy Brisset, Vernon; Michel Mas, Magnanville; Alain Muller, Francheville Le Bas; Jean Peyrot, Le Havre, all of France

[73] Assignees: Compagnie Francaise de Raffinage, Paris; Gamlen Europe S.A., Bougival, both of France

[21] Appl. No.: 559,333

[22] Filed: Dec. 8, 1983

[30] Foreign Application Priority Data

Dec. 10, 1982 [FR] France .................. 82 20783

[51] Int. Cl.$^4$ .................................. C10L 1/18
[52] U.S. Cl. ................................. 44/68; 44/53; 260/414; 534/15; 534/16
[58] Field of Search ............. 44/68, 53; 260/414, 260/429.2, 429 R, 439 R; 252/386

[56] References Cited

U.S. PATENT DOCUMENTS

| 2,460,700 | 2/1949 | Lyons | 44/68 |
| 2,737,932 | 3/1956 | Thomas | 44/68 |
| 3,157,682 | 11/1964 | Ramsden | 44/68 |
| 3,419,587 | 12/1968 | Harson | 260/414 |
| 3,673,229 | 6/1972 | Rinse | 260/429.2 |
| 4,122,107 | 10/1978 | Kenney | 260/414 |
| 4,251,233 | 2/1981 | Sieners et al. | 44/68 |
| 4,264,335 | 4/1981 | Bello et al. | 252/386 |
| 4,337,208 | 6/1982 | Petronella | 260/439 R |
| 4,347,062 | 8/1982 | Born et al. | 44/68 |
| 4,474,580 | 10/1984 | MacKenzie et al. | 44/68 |

FOREIGN PATENT DOCUMENTS

| 2172797 | 10/1973 | France . |
| 2359192 | 2/1978 | France . |
| 2486083 | 1/1982 | France . |

*Primary Examiner*—William R. Dixon, Jr.
*Assistant Examiner*—Margaret B. Medley
*Attorney, Agent, or Firm*—Curtis, Morris & Safford

[57] ABSTRACT

A mixed organometallic composition suitable for use as fuel additives contains an organic acid salt of at least one metal from the lanthanide group and of at least one metal selected from the group formed by manganese and the metals of the iron group wherein the ratio of total number of metal atoms to number of organic acid equivalents is greater then the stoichiometric proportion, and preferably greater than 2.

20 Claims, No Drawings

MIXED ORGANOMETALLIC COMPOSITIONS COMPRISING ELEMENTS FROM THE LANTHANIDE GROUP AND MANGANESE OR ELEMENTS FROM THE IRON GROUP, PROCESS FOR THE PREPARATION OF SAID COMPOSITIONS, AND THEIR USE AS FUEL ADDITIVES

The present invention relates to mixed organometallic compositions comprising elements from the lanthanide group and manganese or elements from the iron group. It further relates to a process for the preparation of said compositions and their use as combustion-improving additives for liquid fuels such as fuel oils or gas oils.

It is already known to use organic iron salts as combustion-improving additives for liquid fuels. These are formed of a complex salt of an organic acid and iron in which the ratio between the number of organic acid equivalents and the number of iron atoms is less than 3 and, more particularly, between $\frac{1}{3}$ and 3. In this connection, reference is made to French patent 2,172,797 to one of the applicants. That patent relates to organometallic compositions of iron in concentrated solution (up to 300 grams/liter of metal) which are not expensive, have a low viscosity, and are easy to handle, store and transport.

By "number of acid equivalents" is meant the number of acid molecules when the acid used is monofunctional. That number must be doubled or tripled in the case of diacids or triacids, respectively, and, more generally, multiplied by the number of acid functions.

It is further known to use organic manganese salts in which the ratio between the number of acid equivalents and the number of manganese atoms is less than 2. (See French Pat. No. 2,486,083 to the same applicant.)

The prior art also describes organic acid salts prepared from rare earths, and particularly from cerium, which are useful as combustion aids and in which the ratio between the number of acid equivalents and the number of cerium atoms is less than the normal stoichiometric proportion and, more particularly, is between 0.2 and 1. (See French Pat. No. 2,359,192, also to the same applicant.) These compounds have the advantage that they are highly concentrated with respect to cerium (up to 800 grams/liter), are less expensive than the "stoichiometric" fatty acid salts, and have viscosity characteristics which make for ease of use.

The doping of fuels with these types of products makes it possible, above all, to reduce the amount of unburned solids during combustion.

In particular, liquid fuels in which cerium salts identical with those described above have been incorporated exhibit markedly improved combustion characteristics, even when combustion takes place with little excess air (less than 1 percent of oxygen), for which the action of iron salts, though sufficient, does not permit optimum results to be obtained.

However, despite the lower cost which the use of organometallic cerium salts entails and which is made possible by the use of an amount of fatty acid that is smaller than the stoichiometric proportion, these products are relatively costly because of the high cost of the mineral salts of rare earths, which is more than eight times the cost or iron, calculated on the basis of the metal.

The present invention proposes synthetic mixed organometallic compounds whose effectiveness as combustion aids is at least on a par with that of salts of cerium alone and whose cost is very much lower than that of those salts.

The present invention thus has as an embodiment mixed organometallic compositions which are characterized in that they comprise organic acid salts of at least one metal from the lanthanide group and of at least one metal selected from the group formed by manganese and the metals of the iron group, and in which the ratio between total number of metal atoms and the number of organic acid equivalents is greater than the stoichiometric proportion, and preferably greater than 2.

Within this definition of an embodiment of the invention and hereinafter in this specification, "element from the iron group" means an element selected from the group formed by iron, cobalt and nickel.

Iron is the preferred element because of its relatively low cost; but the use of cobalt or nickel may also be considered, especially in combination with iron.

The lanthanides may be used alone or in admixture. Since they are difficult to obtain in the pure state, "natural" mixtures may be considered.

In the composition, the lanthanide is preferably used in the +3 oxidation state, although it may also be used in the +4 oxidation state if the latter exists.

The preferred lanthanide is cerium; but lanthanum, neodymium and praseodymium can be used just as successfully.

The relative proportions of the lanthanide and of manganese or of the element from the iron group may be varied on the basis of the ceiling set on the final cost of the product and of the performance to be secured.

The compositions in accordance with the invention preferably comprise from 20 to 85 weight percent of the irongroup metal or of manganese, based on the total weight of the metals, and from 80 to 15 weight percent of the lanthanide.

According to one characteristic of the invention, the organic acid which goes into the compositions of the invention may be selected from among the fatty acids having more than seven carbon atoms, the alkyl, aryl or alkylaryl sulfonic acids, and the carboxylic acids with an alkylaryl chain having more than eight carbon atoms. The compositions may contain one or more acids in admixture.

The organometallic derivatives of the lanthanides and the elements from the iron group are prepared by a process which forms another embodiment of the present invention. Said process consists in reacting the organic acid or a derivative thereof, and more particularly one of its alkali-metal salts, in an organic medium either with a mixture of water-soluble salts of the metals which are coprecipitated in hydroxide form with a strong base such as soda, potassium or ammonia, or successively with the hydroxides of the metals obtained by separate precipitation of the corresponding salts. As a rule, a ratio between the total number of metal atoms and the number of organic acid equivalents greater than 3 and, if desired, as high as 9 should be used; however, said ratio preferably ranges from 3 to 6. The reaction is preferably carried out with the reaction medium being heated and maintained well agitated.

The separation of the water formed by the reaction medium may be facilitated, on completion of the reaction, by the addition of a third solvent, such as glycol, an alcohol or an alkyl glycol. The metal concentrations in the prepared organometallic solutions will depend on the amount of hydrocarbon used as solvent for the organic acid.

The compounds of manganese and of the lanthanides may be obtained by successively reacting the organic acid or a derivative thereof with the manganese hydroxide in an ammoniacal medium, and then with the lanthanide hydroxide obtained by precipitation of the corresponding salt with a strong base, the ratio between metal atoms and acid equivalents ranging from 2 to 8, and preferably from 2 to 4.

Another aim of the invention is to obtain solutions with high metal concentrations (which may be as high as 300 grams/liter in the case of the iron compounds and 350 g/l in the case of the manganese compounds) that will remain fluid and can readily be used in the fuel.

Depending on their concentrations, these various compositions may be added to liquid fuels in such proportions that the latter contain from 10 to 100 ppm of metal. They permit the amount of unburned solids due to incomplete combustion to be reduced, regardless of the excess of air used, and especially when there is little excess air.

The examples which follow will serve to illustrate the invention without limiting it in any way.

EXAMPLES

These examples relate to the preparation of compositions in accordance with the invention and to their use in combustion tests.

The combustion tests which made it possible to demonstrate the effectiveness of the compounds of the invention were conducted in an installation and with a fuel having the following characteristics:

| (1) Heating installation and combustion parameters | |
|---|---|
| Boiler: | 1200 kw |
| Type of burner: | Mechanical return-flow atomization |
| Viscosity of fuel oil to burner: | 15 centistokes |
| Fuel-oil pressure: | 25 bars |
| Flow rate: | 100 kg/hr |
| Variation of excess air: | 1 to 10% of oxygen |
| (2) Fuel No. 2 fuel oil | |
| Sulfur: | 3.9 wt. % (determined by chemical analysis) |
| Asphaltenes: | 6.5 wt. % (determined in conformity with French standard AFNOR T 60-115) |
| Gravity at 15° C.: | 1.006 (French standard AFNOR T 60-101) |
| Viscosity: | 40 centistokes at 100° C. (French standard AFNOR T 60-100) |
| Conradson carbon: | 15 (French standard AFNOR R 60-116) |

The unburned solids were determined in conformity with French standard AFNOR X 44-052.

EXAMPLE 1

1,165 g of a ferric chloride solution of 42.5 degrees Baumé and 171 g of pentahydrated cerous nitrate were precipitated in hydroxide form by adding ammonia until the pH was 8.

The resulting precipitate was washed with water until the $NO_3^-$ and $Cl^-$ anions disappeared and then reacted with 245 g of oleic acid and 560 cm$^3$ of white (petroleum) spirit. The reaction medium was heated to 90° C. and held at that temperature for 3 hours with good agitation. 120 g of the ethyl ether of ethylene glycol was then added to bring about the separation of the water in the lower part.

The last traces of water in the organic solution obtained were removed by atmospheric distillation. The organic solution had a metal content of 230 grams/liter, formed of 173 g/l of iron and 57 g/l of cerium. The ratio between metal atoms and number of acid equivalents was 4.

This solution was added to a fuel oil used to fire the boiler specified above in such measure that the fuel contained 35 ppm of metal. This test was conducted by comparison with two other treatments, one using a ferric oleate, the other a cerium oleate (both prepared in accordance with the patents cited above). The particle-emission rates measured in the combustion gases (expressed as mg/m$^3$ of smoke) are given in Table 1 which follows.

TABLE 1

| | | Particle rate | | |
|---|---|---|---|---|
| Additive used | Concentration of additive used | With 1% oxygen for combustion | With 2% oxygen for combustion | With 5% oxygen for combustion |
| 0 | 0 | 1,180 | 960 | 660 |
| Ferric oleate | 35 ppm iron | 1,010 | 800 | 470 |
| Cerium oleate | 35 ppm cerium | 820 | 640 | 380 |
| Ferric/cerium oleate | 26 ppm iron 9 ppm cerium | 750 | 620 | 300 |

The reduction in the amount of unburned solids obtained with the product of the present invention is greater than that obtained with salts of cerium or iron alone.

As this example shows, the mixed iron and cerium compositions of the invention unexpectedly give better results, with both a small and a large excess of air, than iron or cerium compositions.

EXAMPLE 2

Into 700 cm$^3$ of a gas oil, there were poured, with agitation, 120 g of a mixture of fatty acids known as tall foil and then 180 g of freshly precipitated and washed ferric hydroxide containing about 15% moisture. The reaction medium was heated to 80° C. during 2 hours and then cooled to ambient temperature.

Independently, 180 g of hydrated cerous chloride (6H$_2$O) was dissolved in 200 cm$^3$ of water and the corresponding hydroxide was precipitated with ammonia until the pH was 8, filtered, and washed until the Cl$^-$ and NH$_4^{30}$ ions disappeared.

This hydroxide was gradually added, with agitation, to the above reaction medium, and the temperature was increased to and held at 90° C. for 3 hours. The addition of 30 g of the isopropyl ether of ethylene glycol permitted the water to be separated from the organic phase, and the latter was then purified by distillation.

The resulting product contained 150 g/l of metal, of which 80 g/l was iron and 70 g/l was cerium. The ratio between metal atoms and fatty acid was 5.2, and the product was readily dilutable with both heavy and light hydrocarbons.

The results obtained with this product as a combustion promoter are essentially identical to those given by the product described in Example 1.

EXAMPLE 3

The procedure used in Example 1 was followed, except that in place of the 171 g of pentahydrated cerous nitrate the same amount of tetrahydrated ceric sulfate was used.

The product obtained contained 170 g/l iron and 59.5 g/l cerium, and the ratio between metal atoms and fatty acid was 3.95.

The technical results obtained with this product were the same as those obtained with the product described in Example 1.

EXAMPLE 4

Starting from a mixture of 590 g of tetrahydrated ceric sulfate and 460 g of a ferric chloride solution of 45.2 degrees Baumé, the hydroxides of iron and cerium were coprecipitated by adding ammonia until the pH was 7.5. After washing, the mixture was added, with good agitation and at ambient temperature, to an organic solution formed of 185 g of dodecylbenzenesulfonic acid and 750 cm$^3$ of white (petroleum) spirit. The reaction medium was heated to 90° C. and held at that temperature for 4 hours, and the intrinsic moisture and the water formed in the reaction were then removed by atmospheric distillation, with the temperature increased to 150° C.

The organic solution obtained contained 272 g/l of metal, of which 204 g/l was cerium and 68 g/l was iron. The metal/acid ratio was 4.8.

This product, added to fuel oil at the rate of 35 ppm of metal (26 ppm Ce and 9 ppm Fe) under the conditions specified in Example 1, gave the results presented in Table 2 which follows.

TABLE 2

| Additive used | Concentration of additive used | Particle rate | | |
|---|---|---|---|---|
| | | With 1% oxygen for combustion | With 2% oxygen for combustion | With 5% oxygen for combustion |
| 0 | 0 | 1,180 | 960 | 660 |
| Iron/cerium sulfonate | 26 ppm iron 9 ppm cerium | 800 | 640 | 350 |

This table demonstrates the effectiveness of the compositions of the invention.

EXAMPLE 5

130 g of heptahydrated lanthanum chloride and 390 g of anhydrous ferric chloride were dissolved in one liter of water with agitation. A 20% ammonia solution was then added until the pH was 8.5. The precipitate obtained was filtered and washed and then incorporated in a mixture of 205 g of linoleic acid dissolved in 720 cm$^3$ of a gas oil. The reaction medium was heated to 90° C. during 4 hours. Separation of the organic and aqueous phases after the reaction was facilitated by the addition of 40 g of the butyl ether of ethylene glycol. The reddish organic complex obtained was purified.

Its metal content was 180 g/l, of which 133 g was iron and 47 g was lanthanum. It was readily diluted with hydrocarbons, and the metal/fatty acid ratio was 4.1.

EXAMPLE 6

The procedure used in Example 5 was followed, except that in place of the 130 g of lanthanum chloride 142 g of monohydrated neodymium acetate was used. The product obtained contained 195 g/l of metal, of which 135 g/l was iron and 60 g/l was neodymium. The metal/acid ratio was 4.3.

EXAMPLE 7

260 g of technical oleic acid (acid value, 193, as determined in conformity with French standard AFNOR T 66-013) was dissolved in 750 cm$^3$ of white (petroleum) spirit. 870 g of tetrahydrated manganese acetate and 1,200 cm$^3$ of ammonia of 20 degrees Baumé were then gradually added with agitation. The temperature of the reaction medium was approximately 45° C. on completion of such addition.

The temperature of the reaction medium was raised to 55° C. with vigorous agitation during 5 hours, and then to 85° C., to break the emulsion formed by the organic and aqueous phases. The decanted water was separated from the reaction medium.

The cerous hydroxide obtained by precipitation with ammonia from 160 g of cerous nitrate, filtration and washing with water was then dispersed in the organic phase. The temperature of the reaction medium was raised to 90° C. with vigorous agitation during 2 hours. The water was removed by decantation and evaporation. An organic solution with a metal content of 203 g/l was so obtained, 160 g/l being manganese, and 43 g/l, cerium. The ratio between metal atoms and number of acid equivalents was 3.2.

This solution was added to fuel oil used to fire the boiler described earlier in such measure that the fuel contained 35 ppm of metal. The test was conducted by comparison with two other treatments, one with a manganese oleate, the other with a cerium oleate. The particle emission rates measured in the combustion gases (expressed as mg/m$^3$ of smoke) are given in Table 3 which follows.

TABLE 3

| Additive used | Concentration of additive used | Particle rate | | |
|---|---|---|---|---|
| | | With 1% oxygen for combustion | With 2% oxygen for combustion | With 5% oxygen for combustion |
| 0 | 0 | 1,180 | 960 | 660 |
| Manganese oleate | 35 ppm manganese | 990 | 800 | 480 |
| Cerium oleate | 35 ppm cerium | 820 | 640 | 380 |
| Manganese/cerium | 28 ppm manganese | 740 | 600 | 350 |

TABLE 3-continued

| Additive used | Concentration of additive used | Particle rate | | |
|---|---|---|---|---|
| | | With 1% oxygen for combustion | With 2% oxygen for combustion | With 5% oxygen for combustion |
| oleate | 7 ppm cerium | | | |

The reduction in the amount of unburned solids obtained with the product of the present invention is greater than that obtained with the salts of cerium or manganese alone.

As this example shows, the mixed manganese and cerium compositions of the invention unexpectedly give better results, with both a small and a large excess of air, than manganese or cerium compositions.

We claim:

1. A mixed organometallic composition, which comprises an organic acid salt of at least one metal from the lanthanide group and of at least one metal selected from the group consisting of manganese and the metals of the iron group, wherein the ratio of the total number of metal atoms to the number of organic acid equivalents is greater than the stoichiometric proportion.

2. A composition according to claim 1, wherein the ratio of the total number of metal atoms to the number of organic acid equivalents is greater than 2.

3. A composition according to claim 1, wherein the metal from the iron group is iron.

4. A composition according to claim 1, wherein the metal from the lanthanide group is selected from the group consisting of cerium, lanthanum, neodymium and praseodymium.

5. A composition according to claim 1, wherein the metal from the lanthanide group is cerium.

6. A composition according to claim 1, wherein the amount of metal from the iron group is from 20 to 85 weight percent and of metal from the lanthanide group is from 80 to 15 weight percent based on the total weight of the metals.

7. A composition according to claim 1, wherein the organic acid is selected from the group consisting of fatty acids having more than seven carbon atoms, alkyl, aryl or alkylaryl sulfonic acids, and carboxylic acids with an alkylaryl chain having more than eight carbon atoms.

8. A composition according to claim 1, wherein the ratio of the total number of metal atoms to the number of organic acid equivalents is greater than 2, the metal from the iron group is iron, the metal from the lanthanide group is cerium, the amount of metal from the iron group is from 20 to 85 weight percent and of metal from the lanthanide group is from 80 to 15 weight percent based on the total weight of the metals, and the organic acid is selected from the group consisting of fatty acids having more than seven carbon atoms, alkyl, aryl or alkylaryl sulfonic acids, and carboxylic acids with an alkylaryl chain having more than eight carbon atoms.

9. A process for the preparation of a mixed organometallic composition containing an organic acid salt of at least one metal from the iron group and of at least one metal from the lanthanide group, which comprises reacting an organic acid or a derivative thereof in an organic medium either with a mixture of hydroxides of the metals from the iron and lanthanide groups obtained by coprecipitation, or successively with the hydroxides of these metals obtained by separate precipitation.

10. A process according to claim 9, wherein the ratio of total metal atoms to number of organic acid equivalents range from 3 to 9.

11. A process according to claim 9, wherein the ratio of total metal atoms to number of organic acid equivalents range from 3 to 6.

12. A process according to claim 9, further comprising adding a solvent such that separation of water formed is facilitated.

13. A process according to claim 12, wherein the solvent is a glycol, an alcohol or an alkyl glycol.

14. A mixed organometallic composition comprising an organic acid salt of at least one metal from the iron group and of at least one metal from the lanthanide group prepared by a process according to claim 9.

15. A process for the preparation of mixed organometallic compositions containing an organic acid salt of at least one lanthanide and of manganese, which comprises reacting an organic acid or a derivative thereof successively with manganese hydroxide in an ammoniacal medium and then with lanthanide hydroxide.

16. A process according to claim 15, wherein the ratio of total metal atoms to number of organic acid equivalents ranges from 2 to 8.

17. A process according to claim 15, wherein the ratio of total metal atoms to number of organic acid equivalents ranges from 2 to 4.

18. A mixed organometallic composition comprising an organic acid salt of at least one lanthanide and of manganese, prepared by a process according to claim 15.

19. A process for improving combustion of fuel, which comprises adding a composition as recited in claim 1.

20. A process according to claim 19, wherein the composition is added in a concentration of from 10 to 100 ppm of metal.

* * * * *